United States Patent
Kelly et al.

(10) Patent No.: US 7,601,174 B2
(45) Date of Patent: Oct. 13, 2009

(54) WEAR-RESISTANT ENDOPROSTHETIC DEVICES

(75) Inventors: Aaron Kelly, Snoqualmie, WA (US); Leonard Tokish, Issaquah, WA (US); Jeff Edfast, Duvall, WA (US); David Yager, Monroe, WA (US); Alex Kunzler, Issaquah, WA (US); Vincent Bryan, Mercer Island, WA (US); Randy Allard, Germantown, TN (US); Jeff Rouleau, Redmond, WA (US); Robert Conta, Mercer Island, WA (US); Carlos Gil, Sammamish, WA (US)

(73) Assignee: Warsaw Orthopedic, Inc.

( * ) Notice: Subject to any disclaimer, the term of this patent is extended or adjusted under 35 U.S.C. 154(b) by 490 days.

(21) Appl. No.: 10/600,052

(22) Filed: Jun. 20, 2003

(65) Prior Publication Data

US 2004/0054411 A1   Mar. 18, 2004

Related U.S. Application Data

(63) Continuation-in-part of application No. 09/923,891, filed on Aug. 7, 2001, now Pat. No. 6,949,105, which is a continuation-in-part of application No. 09/783,860, filed on Feb. 13, 2001, now abandoned, application No. 10/600,052, which is a continuation-in-part of application No. 09/924,298, filed on Aug. 8, 2001, which is a continuation-in-part of application No. 09/783,910, filed on Feb. 13, 2001, now abandoned.

(60) Provisional application No. 60/265,218, filed on Jan. 31, 2001, provisional application No. 60/223,863, filed on Aug. 8, 2000.

(51) Int. Cl.
*A61F 2/44* (2006.01)

(52) U.S. Cl. .................. 623/17.13; 623/17.15

(58) Field of Classification Search ... 623/17.11–17.16, 623/23.54, 23.51, 23.58, 23.59, 23.63, 23.61
See application file for complete search history.

(56) References Cited

U.S. PATENT DOCUMENTS 2,677,369 A    5/1954   Knowles (Continued)

FOREIGN PATENT DOCUMENTS

DE    2263842    7/1974

(Continued)

OTHER PUBLICATIONS

Brain, et al., "The Neurological Manifestations of Cervical Spondylosis", Brain: A Journal of Neurology, vol. 75; Macmillan & Co.; 1952; pp. 187-225.

(Continued)

*Primary Examiner*—Pedro Philogene

(57) ABSTRACT

An implantable endoprosthesis is adapted to articulate with one or more prosthesis surfaces, and is at least partially formed from a material having high wear resistance, which may be a polymeric material such as ultra-high molecular weight polyethylene (UHMWPE), polyetherether ketone (PEEK), and the like, or a metallic material, such as a cobalt-chrome alloy, or a ceramic material, such as alumina or zirconia. The body member of the endoprosthesis may be formed from a composite material, and includes at least a first component formed from a first material having increased wear resistance as compared to that of a second material forming a second component of the body member. The second material is generally more resilient as compared to the first material.

20 Claims, 3 Drawing Sheets

U.S. PATENT DOCUMENTS

| | | |
|---|---|---|
| 3,486,505 A | 12/1969 | Morrison |
| 3,574,374 A | 4/1971 | Keller et al. |
| 3,864,758 A | 2/1975 | Yakich |
| 3,875,595 A | 4/1975 | Froning |
| 3,876,728 A | 4/1975 | Stubstad |
| 4,023,572 A | 5/1977 | Weigand et al. |
| 4,116,200 A | 9/1978 | Braun et al. |
| 4,179,810 A | 12/1979 | Kirsch |
| 4,193,139 A | 3/1980 | Walker |
| 4,309,777 A | 1/1982 | Patil |
| 4,313,232 A | 2/1982 | Habal et al. |
| 4,314,380 A | 2/1982 | Miyata et al. |
| 4,349,921 A | 9/1982 | Kuntz |
| 4,359,318 A | 11/1982 | Gittleman |
| 4,599,086 A | 7/1986 | Doty |
| 4,645,507 A | 2/1987 | Engelbrecht et al. |
| 4,714,469 A | 12/1987 | Kenna |
| 4,743,256 A | 5/1988 | Brantigan |
| 4,757,983 A | 7/1988 | Ray et al. |
| 4,759,766 A | 7/1988 | Buettner-Janz et al. |
| 4,759,769 A | 7/1988 | Hedman et al. |
| 4,766,328 A | 8/1988 | Yang |
| 4,777,942 A | 10/1988 | Frey et al. |
| 4,800,639 A | 1/1989 | Frey et al. |
| 4,834,757 A | 5/1989 | Brantigan |
| 4,863,476 A | 9/1989 | Shepperd |
| 4,863,477 A | 9/1989 | Monson |
| 4,874,389 A | 10/1989 | Downey |
| 4,878,915 A | 11/1989 | Brantigan |
| 4,887,595 A | 12/1989 | Heinig et al. |
| 4,904,260 A | 2/1990 | Ray et al. |
| 4,904,261 A | 2/1990 | Dove et al. |
| 4,908,032 A | 3/1990 | Keller |
| 4,908,036 A | 3/1990 | Link et al. |
| 4,911,718 A | 3/1990 | Lee et al. |
| 4,917,704 A | 4/1990 | Frey et al. |
| 4,932,969 A | 6/1990 | Frey et al. |
| 4,932,975 A | 6/1990 | Main et al. |
| 4,946,378 A | 8/1990 | Hirayama et al. |
| 4,955,908 A | 9/1990 | Frey et al. |
| 4,978,355 A | 12/1990 | Frey et al. |
| 4,990,163 A | 2/1991 | Ducheyne et al. |
| 4,997,432 A | 3/1991 | Keller |
| 5,002,576 A | 3/1991 | Fuhrmann et al. |
| 5,015,247 A | 5/1991 | Michelson |
| 5,035,716 A | 7/1991 | Downey |
| 5,047,055 A | 9/1991 | Bao et al. |
| 5,059,193 A | 10/1991 | Kuslich |
| 5,059,194 A | 10/1991 | Michelson |
| 5,062,845 A | 11/1991 | Kuslich et al. |
| 5,071,437 A | 12/1991 | Steffee |
| 5,080,662 A | 1/1992 | Paul |
| 5,084,048 A | 1/1992 | Jacob et al. |
| 5,108,438 A | 4/1992 | Stone |
| 5,122,130 A | 6/1992 | Keller |
| 5,123,926 A | 6/1992 | Pisharodi |
| 5,171,280 A | 12/1992 | Baumgartner |
| 5,171,281 A | 12/1992 | Parsons et al. |
| 5,176,708 A | 1/1993 | Frey et al. |
| 5,192,326 A | 3/1993 | Bao et al. |
| 5,192,327 A | 3/1993 | Brantigan |
| 5,201,749 A | 4/1993 | Sachse et al. |
| 5,207,680 A | 5/1993 | Dietz et al. |
| 5,219,363 A | 6/1993 | Crowninshield et al. |
| 5,234,431 A | 8/1993 | Keller |
| 5,236,460 A | 8/1993 | Barber |
| 5,246,458 A | 9/1993 | Graham |
| 5,257,998 A | 11/1993 | Ota et al. |
| 5,258,031 A | 11/1993 | Salib et al. |
| 5,261,911 A | 11/1993 | Carl |
| 5,261,913 A | 11/1993 | Marnay |
| 5,306,308 A | 4/1994 | Gross et al. |
| 5,314,477 A | 5/1994 | Marnay |
| 5,314,478 A | 5/1994 | Oka et al. |
| 5,320,644 A | 6/1994 | Baumgartner |
| 5,370,697 A * | 12/1994 | Baumgartner ............ 623/17.15 |
| 5,383,933 A | 1/1995 | Keller |
| 5,389,101 A | 2/1995 | Heilbrun et al. |
| 5,401,269 A * | 3/1995 | Buttner-Janz et al. .... 623/17.15 |
| 5,403,314 A | 4/1995 | Currier |
| 5,425,772 A | 6/1995 | Brantigan |
| 5,425,773 A | 6/1995 | Boyd et al. |
| 5,443,514 A | 8/1995 | Steffee |
| 5,456,719 A | 10/1995 | Keller |
| 5,458,638 A | 10/1995 | Kuslich et al. |
| 5,458,642 A | 10/1995 | Beer et al. |
| 5,484,437 A | 1/1996 | Michelson |
| 5,486,180 A | 1/1996 | Dietz et al. |
| 5,489,307 A | 2/1996 | Kuslich et al. |
| 5,489,308 A | 2/1996 | Kuslich et al. |
| 5,496,318 A | 3/1996 | Howland et al. |
| 5,507,816 A | 4/1996 | Bullivant |
| 5,514,180 A | 5/1996 | Heggeness et al. |
| 5,527,315 A | 6/1996 | Jeanson et al. |
| 5,534,005 A | 7/1996 | Tokish, Jr. et al. |
| 5,534,028 A | 7/1996 | Bao et al. |
| 5,534,029 A | 7/1996 | Shima |
| 5,534,030 A | 7/1996 | Navarro et al. |
| 5,545,229 A | 8/1996 | Parsons et al. |
| 5,549,679 A | 8/1996 | Kuslich |
| 5,556,431 A | 9/1996 | Buttner-Janz |
| 5,562,738 A | 10/1996 | Boyd et al. |
| 5,571,189 A | 11/1996 | Kuslich |
| 5,593,409 A | 1/1997 | Michelson |
| 5,593,445 A | 1/1997 | Waits |
| 5,609,636 A | 3/1997 | Kohrs et al. |
| 5,641,323 A | 6/1997 | Caldarise |
| 5,645,597 A | 7/1997 | Krapiva |
| 5,645,598 A | 7/1997 | Brosnahan |
| 5,649,926 A | 7/1997 | Howland |
| 5,653,714 A | 8/1997 | Dietz et al. |
| 5,658,285 A | 8/1997 | Marnay et al. |
| 5,662,158 A | 9/1997 | Caldarise |
| 5,674,294 A * | 10/1997 | Bainville et al. ......... 623/17.16 |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,702,450 A | 12/1997 | Bisserie |
| 5,713,899 A | 2/1998 | Marnay et al. |
| 5,716,415 A | 2/1998 | Steffee |
| 5,720,748 A | 2/1998 | Kuslich et al. |
| 5,722,977 A | 3/1998 | Wilhelmy |
| 5,723,013 A | 3/1998 | Jeanson et al. |
| 5,741,253 A | 4/1998 | Michelson |
| 5,782,830 A | 7/1998 | Farris |
| 5,782,832 A * | 7/1998 | Larsen et al. ............ 623/17.11 |
| 5,797,909 A | 8/1998 | Michelson |
| 5,824,093 A | 10/1998 | Ray et al. |
| 5,824,094 A * | 10/1998 | Serhan et al. ............ 623/17.16 |
| 5,865,846 A | 2/1999 | Bryan et al. |
| 5,865,848 A | 2/1999 | Baker |
| 5,868,796 A | 2/1999 | Buechel et al. |
| 5,885,300 A | 3/1999 | Tokuhashi et al. |
| 5,888,197 A | 3/1999 | Mulac et al. |
| 5,888,226 A | 3/1999 | Rogozinski |
| 5,897,087 A | 4/1999 | Farley |
| 5,902,233 A | 5/1999 | Farley et al. |
| 5,928,284 A | 7/1999 | Mehdizadeh |
| 5,947,971 A | 9/1999 | Kuslich et al. |
| 5,964,761 A | 10/1999 | Kambin |
| 5,976,187 A | 11/1999 | Richelsoph |
| 5,984,865 A | 11/1999 | Farley et al. |
| 5,989,291 A | 11/1999 | Ralph et al. |

| | | |
|---|---|---|
| 6,001,130 A | 12/1999 | Bryan et al. |
| 6,017,008 A | 1/2000 | Farley |
| 6,022,376 A | 2/2000 | Assell |
| 6,033,363 A | 3/2000 | Farley et al. |
| 6,059,790 A | 5/2000 | Sand et al. |
| 6,059,829 A | 5/2000 | Schlapfer et al. |
| 6,063,121 A | 5/2000 | Xavier et al. |
| 6,066,174 A | 5/2000 | Farris |
| 6,080,155 A | 6/2000 | Michelson |
| 6,083,228 A | 7/2000 | Michelson |
| 6,086,595 A | 7/2000 | Yonemura et al. |
| 6,096,038 A | 8/2000 | Michelson |
| 6,096,084 A | 8/2000 | Townley |
| 6,132,465 A | 10/2000 | Ray et al. |
| 6,139,579 A | 10/2000 | Steffee et al. |
| 6,146,421 A * | 11/2000 | Gordon et al. ............ 623/17.15 |
| 6,156,067 A | 12/2000 | Bryan et al. |
| 6,162,252 A | 12/2000 | Kuras et al. |
| 6,179,874 B1 | 1/2001 | Cauthen |
| 6,228,022 B1 | 5/2001 | Friesem et al. |
| 6,228,026 B1 | 5/2001 | Rull et al. |
| 6,231,609 B1 | 5/2001 | Mehdizadeh |
| 6,261,293 B1 * | 7/2001 | Nicholson et al. ............ 606/82 |
| 6,283,998 B1 | 9/2001 | Eaton |
| 6,290,726 B1 * | 9/2001 | Pope et al. ............... 623/22.15 |
| 6,348,071 B1 | 2/2002 | Steffee et al. |
| 6,395,032 B1 | 5/2002 | Gauchet |
| 6,395,034 B1 * | 5/2002 | Suddaby ................. 623/17.15 |
| 6,402,785 B1 | 6/2002 | Zdeblick et al. |
| 6,419,706 B1 * | 7/2002 | Graf ........................ 623/17.16 |
| 6,436,101 B1 | 8/2002 | Hamada |
| 6,517,544 B1 | 2/2003 | Michelson |
| 6,533,817 B1 | 3/2003 | Norton et al. |
| 6,533,818 B1 * | 3/2003 | Weber et al. ............. 623/17.16 |
| 6,575,899 B1 | 6/2003 | Foley et al. |
| 6,582,466 B1 | 6/2003 | Gauchet |
| 6,682,562 B2 * | 1/2004 | Viart et al. ............... 623/17.14 |
| 7,025,787 B2 | 4/2006 | Bryan et al. |
| 2002/0151901 A1 | 10/2002 | Bryan et al. |
| 2002/0183848 A1 | 12/2002 | Ray et al. |
| 2004/0158254 A1 | 8/2004 | Eisermann |

FOREIGN PATENT DOCUMENTS

| | | | |
|---|---|---|---|
| DE | 2804936 | | 8/1979 |
| DE | 30 23 353 A1 | | 4/1981 |
| DE | 3343863 A1 | | 6/1985 |
| DE | 37 41 493 A1 | | 6/1989 |
| DE | 9000094.3 U1 | | 1/1990 |
| DE | 90 00 094.3 | | 3/1991 |
| DE | 196 53 580 | | 6/1998 |
| EP | 0176728 | | 4/1986 |
| EP | 0 560 140 A1 | | 9/1993 |
| FR | 2805985 | * | 3/2000 ............ 623/17.14 |
| SU | 895433 | | 1/1982 |
| SU | 1560184 | | 4/1990 |
| WO | 9316656 A2 | | 9/1993 |
| WO | WO 00/04839 | | 2/2000 |
| WO | WO 00/04851 | | 2/2000 |
| WO | WO 00/13619 | | 3/2000 |
| WO | WO 00/13620 | | 3/2000 |
| WO | WO 02 11633 | | 2/2002 |

OTHER PUBLICATIONS

Buttner-Janz, et al.; "Biomechanics of the SB Charite Lumbar Intervertebral Disc Endoprosthesis"; International Orthopedics; vol. 13; 1989; pp. 173-176.

Edeland; "Some Additional Suggestions for an Intervertebral Disc Prosthesis"; Dept. of Occupational Health; Vdvo PV AB; S-40508; Goteborg; Sweden; 1985 Butterworth & Co. Publishers Ltd.

Enker et al.; "Artificial Disc Replacement"; Spine; vol. 18; No. 8, 1993; pp. 1061-1070.

Hawkins, et al.; "Shear Stability of an Elastomeric Disk Spacer Within an Intervertebral Joint: A Parametric Study"; Journal of Biomechanical Engineering Technical Briefs; vol. 114; Aug. 1992; pp. 414-415.

Hedman, et al.; "Design of an Intevertebral Disc Prosthesis"; Spine; vol. 17; No. 6; 1991; pp. S256-S260.

Hellier, et al.; "Wear Studies for Development of an Intervertebral Disc Prosthesis"; Spine; vol. 17; No. 6 Supplement; 1992; S86-S96.

Hood; "Far Lateral Lumbar Disc Herniations"; Neurosurgery Clinics of North America; vol. 4, No. 1; Jan. 1993; pp. 117-124.

Langrana, et al.; "Finite-Element Modeling of the Synthetic Intervertebral Disc"; Spine; vol. 16; No. 6: 1991; pp. S245-S252.

Lee, et al.; "Development of a Prosthetic Intervertebral Disc"; Spine; vol. 16; No. 6; 1991; pp. S253-S255.

Lees, et al.; "Natural History & Prognosis of Cervical Spondylosis"; British Medical Journal; Dec. 28, 1963; British Medical Association, London, England; Copyright 1963; pp. 1607-1610.

Long; "Failed Back Surgery Syndrome"; Neurosurgery Clinics of North America; vol. 2, No. 4; Oct. 1991; pp. 899-919.

Ray; "The Artificial Disc-Introduction, History and Socioeconomics"; Clinical Efficacy and Outcome in the Diagnosis and Treatment of Low Back Pain; Raven Press, Ltd., NY; 1992; pp. 205-280.

Robinson, et al.; "The Results of Anterior Interbody Fusion of the Cervical Spine"; The Journal of Bone & Joint Surgery; vol. 44-A, No. 8, Dec. 1962; pp. 1569-1587.

Simeone and Rothman; "Cervical Disc Disease"; Pennsylvania Hospital & University of Pennsylvania; 1975; pp. 387-433.

Solini, et al.; "Metal Cementless Prosthesis for Vertebral Body Replacement of Metastatic Malignant Disease of the Cervical Spine"; Journal of Spinal Disorders; vol. 2; No. 4; 1989; pp. 254-262.

Taylor, Collier, "The Occurrence of Optic Neuritis in Lesions of the Spinal Cord, Injury, Tumor, Melitis"; Brain: A Journal of Neurology; vol. 24; Macmillian & Co. Ltd, 1901; pp. 532-550.

Tie-sheng, et al.; "Lumbar Intervertebral Disc Prosthesis"; Chinese Medical Journal. 104-(5); 1991; pp. 381-386.

Artificial Disc, Market Potential and Technology update, Viscogliosi Bros., LLC, Feb. 2000, pp. 1-65.

Boning-Up, The Musculoskeletal Healthcare Industry, Industry Commentary & Review of 1999, Viscogliosi Bros., LLC., Mar. 10, 2000, pp. 1-33.

Bryan Total Cervical Disc Prosthesis, Single Level Surgical Technique Manual, Spinal Dynamics Corporation, 2000, 01080-004, pp. 29.

Spine Industry Dynamics, Viscogliosi Bros., LLC., Mar. 10, 2000, pp. 1-4.

Dowson, D., New Joints for the Millennium: wear control in total replacement hip joints, School of Mechanical Engineering, University of Leeds, Leeds, LS2 9JT, UK, IMechE, Jan. 5, 2001, 24 pages.

International Search Report for International Application No. PCT/US01/24791, Sep. 12, 2002, 2 pages.

* cited by examiner

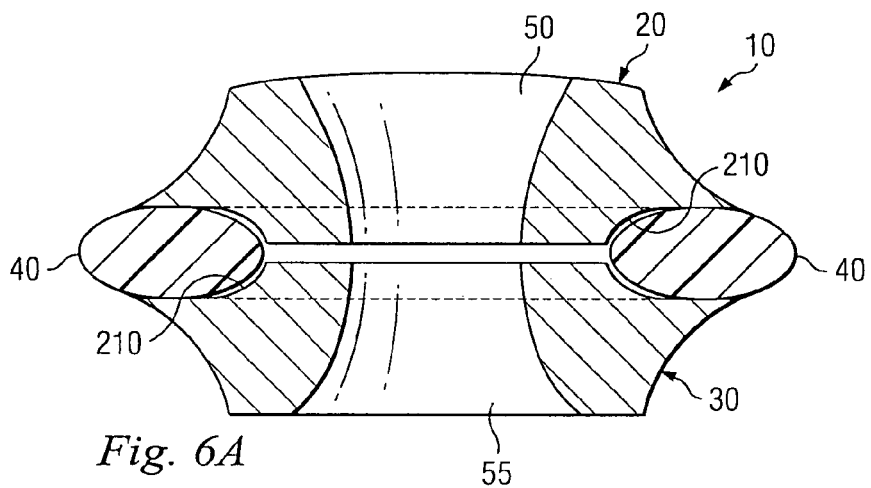
Fig. 6A
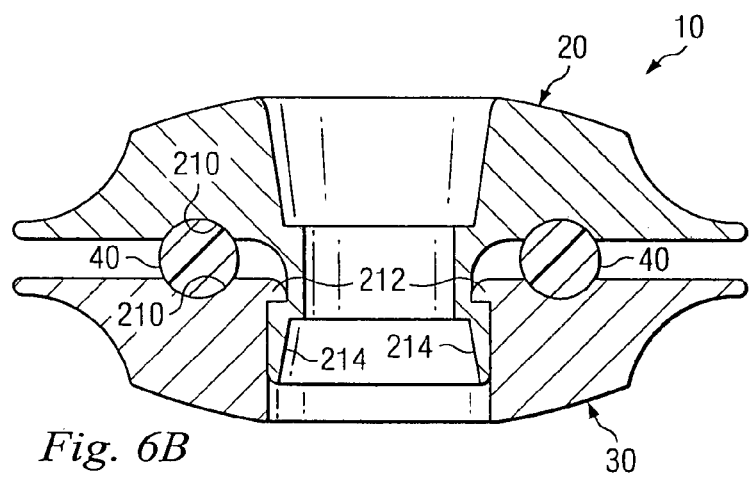
Fig. 6B
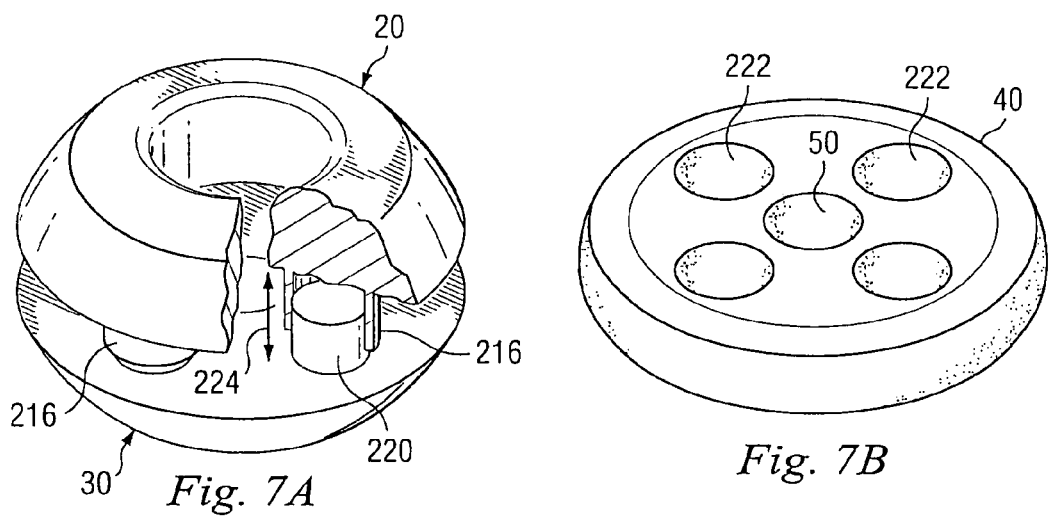
Fig. 7A
Fig. 7B

WEAR-RESISTANT ENDOPROSTHETIC DEVICES

CROSS REFERENCE

This application is a continuation-in-part of U.S. application Ser. No. 09/923,891, filed Aug. 7, 2001 now U.S. Pat. No. 6,949,105, which is a continuation-in-part of U.S. application Ser. No. 09/783,860, filed Feb. 13, 2001, now abandoned which claims benefit to U.S. application Ser. Nos. 60/223,863 filed Aug. 8, 2000 and 60/265,218 filed Jan. 31, 2001. This application is also a continuation-in-part of U.S. application Ser. No. 09/924,298, filed Aug. 8, 2001, which is a continuation-in-part of U.S. application Ser. No. 09/783,910, filed Feb. 13, 2001 now abandoned, which claims benefit to U.S. application Ser. No. 60/223,863 filed Aug. 8, 2000 and 60/265,218 filed Jan. 31, 2001. The entire contents of Ser. Nos. 09/924,298 and 09/923,891 are incorporated herein by reference.

FIELD OF THE INVENTION

The present invention relates generally to prosthetic devices, in particular, to articulated endoprosthetic devices, such as those suitable for implantation in skeletal joints.

BACKGROUND

The need for endoprostheses (prostheses that are implantable) in human joints may arise from degeneration of the joint due to disease or wear, or as the result of fracture of one or more bones forming the joint. The endoprosthesis replaces one or more elements of the joint, frequently providing an artificial surface to bear against another element of the joint, or an element of the prosthesis.

Because many endoprosthesis designs involve surfaces that articulate with respect to each other, these surfaces are subject to wear, i.e., to removal of material from the surfaces as the result of contact with, and movement with respect to, other surfaces in the joint. This wear can generate material known as "wear debris," which are small particles of material that, in some cases cause health problems if released into the body. Some wear debris results from normal contact between surfaces of an articulating endoprosthesis during conditions of use, such as movement between the bearing surfaces of the endoprosthesis. Wear debris can also result from impact between elements of the endoprosthesis, either during normal use conditions, or during more extreme conditions, such as conditions subjecting the joint to unusual movement or shocks. Wear debris can also result from frequent movement of the endoprosthesis beyond its designed range of motion and from multiple components wearing against each other.

Wear debris particles can be found in macrophages (if the debris particles are small enough in size), or in tissue near or around the prosthesis. Inflammatory tissue responses to wear debris (perhaps enabled by inflammatory mediators released by the macrophages) are believed to contribute to bone resorption and some forms of prosthetic loosening, and thus to the resulting need for revision surgery. The amount and type of wear debris generated by various endoprosthesis designs is a parameter that is evaluated in assessing whether such designs should be approved for use.

The degree to which a design may generate wear debris is therefore a parameter that must be balanced against other design considerations for the device. These include materials biocompatibility, mechanical/physical properties, geometry of the endoprosthesis, manufacturing considerations, and the like.

It is also desirable to allow the endoprosthesis to withstand heavy loading while retaining excellent wear and load supporting characteristics, inter alia, in order to make the design more suitable for use in the lumbar region of the spine, where loads are significantly higher than in the cervical spine.

SUMMARY

This invention relates to a body member for an implantable endoprosthesis. In one embodiment, the implantable endoprosthesis is adapted to articulate with one or more prosthesis surfaces, which is at least partially formed from a material having high wear resistance, which may be a polymeric material, such as ultra-high molecular weight polyethylene (UHMWPE), which may be crosslinked or uncrosslinked, polyetherether ketone (PEEK), and the like, or a metallic material, such as a cobalt-chrome alloy, or a ceramic material, such as alumina or zirconia.

In another embodiment, the body member of the endoprosthesis may be formed from a composite material, and contains at least a first component formed from a first material, which has increased wear resistance as compared to that of a second material forming a second component of the body member. The second material is generally more resilient (i.e., has greater elasticity, increased damping, or both) as compared to the first material. The first material is also typically more lubricious and often harder than the second material.

In a specific embodiment, the body member is composed of two materials having a central component formed from the second material disposed between two outer components formed from the first material.

In another specific embodiment, the body member is a composite material having a central component formed from the first material disposed between or around at least one outer component formed from the second material. Additional layers of a wear resistant material, e.g., additional layers of the first material or another material more wear resistant than the second material, can be disposed on one or more outer surfaces of the second material.

The embodiments allow for the construction of an implantable endoprosthesis having one or more elements that articulate relative to the body member of the endoprosthesis such that the surfaces of the body member that have the highest degree of moving contact with other surfaces (and thus more likely to encounter conditions that can generate wear debris) have a high lubricity and wear resistance. Portions of the body member unlikely to encounter significant contact and motion with other endoprosthetic surfaces can be chosen from among materials that provide high resiliency (high elasticity and/or damping).

The invention also relates to a surgical procedure and instruments for implanting the endoprosthesis of the invention, and to a method of implanting an endoprosthesis into a joint, including: obtaining surgical access to the interior of the joint, preparing the interior of the joint to receive an implantable endoprosthesis, introducing the implantable endoprosthesis described above into the interior of the joint.

BRIEF DESCRIPTION OF DRAWINGS

The invention can be more clearly understood by reference to the drawings as described below. The drawings are intended to be illustrative, and not limiting, of the scope of the invention.

FIG. 5A shows a central body having two outer elements of highly wear resistant material surrounding a central element of a resilient elastomeric material. FIG. 5B shows a central body similar to that of FIG. 5A, but schematically illustrates a variety of retention features not shown in FIG. 5A, and providing greater thickness of elastomer between the outer elements.

FIG. 6A is a cross-sectional view of another alternative embodiment of the composite central body having relatively large outer elements and a central element made of an elastomeric O-ring. FIG. 6B is a cross-sectional view of a modification of the embodiment of FIG. 6A, containing outer elements that are adapted to be snap fit and held in place by the compressive force exerted by the O-ring (not shown).

FIG. 7A is a perspective view of the outer elements of another embodiment of a composite central body of an endoprosthesis according to the invention. FIG. 7B is a perspective view of the central element corresponding to the outer elements shown in FIG. 7A.

DETAILED DESCRIPTION

Figure 1:
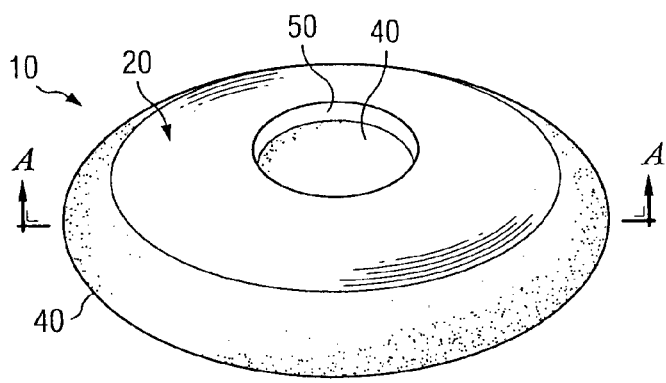
FIG. 1 is a perspective view of one embodiment of a composite central body of an endoprosthesis according to the invention.

In one embodiment of the invention, the central body of the endoprosthesis contains a first component, formed from a first material having higher wear resistance than a second material, which forms a second component of the body member of the endoprosthesis. The second material will generally have a higher resiliency or elasticity than the first material.

In general, the first material will be harder than the second material, as harder materials tend to have better wear resistance than softer materials. In addition, the first material will tend to be very lubricious, typically as lubricious or more lubricious than the second material. However, hardness is not an absolute prerequisite to increased wear resistance, which can result from a number of different factors. It is possible for the two materials to have similar hardnesses, but very different wear resistances, due to other factors such as lubricity, grain structure, wettability, and the like.

In effect, the first material is used to form one or more components of the body member of the endoprosthesis that are designed to contact other elements of the endoprosthesis during articulation. This contact has the potential to generate wear debris, and this potential is decreased by employing the wear resistant first material at the articulation surfaces of the body member.

In general, the second material has high resiliency, and is used to form other components of the body member where high wear resistance is not as critical, because the likelihood of contact with other surfaces under is low. The second material provides beneficial elasticity and dampening effects to the endoprosthesis, and absorbs compressive and shear forces encountered by the endoprosthesis after implantation. In addition, the second material can be used in areas of the endoprosthesis that are likely to undergo vibration or impact with other elements of the endoprosthesis, but unlikely to experience surface, articulating wear. The higher resiliency and generally lower hardness of the second material can decrease the level of wear debris generated from impact.

The first material may be selected from a range of biocompatible materials that provide resistance to formation of wear debris under conditions that the endoprosthesis will encounter after implantation. Suitable materials will, of necessity, depend somewhat on the geometry of the endoprosthesis, the materials selected for other endoprosthesis components (in particular those that will articulate with the body member of the endoprosthesis), the magnitude and/or direction of stresses expected to be encountered by the endoprosthesis, and other factors.

In a particular embodiment, the endoprosthesis contains a central body disposed between two endplates or "shells" that articulate with respect to the central body. The shells may be formed of metals, polymeric materials, ceramics, or combinations thereof. The shells are formed so as to contact the existing elements of the joint, in particular, the ends of the bones of the joint, in a way that the shells are substantially immobilized with respect to the bones of the joint. The bones and the attached shells move together with respect to the central body as the shells articulate with respect to the central body. As an example, the shells can be formed from titanium or other biocompatible metal or alloy, and may have a porous coating formed on one or more outer surfaces thereof, so as to promote fixation via bone growth into the porous coating.

Desirably, the inner surfaces of the shells have been treated to make them smooth, increase their lubricity, or both. For example, the interior surfaces may be polished, coated, or comprise inserts of material different from the remainder of the shell, in order to provide a smooth, wear resistant surface and decrease the likelihood of generating wear debris during articulation.

In this embodiment, the first material may be any material that will exhibit high wear resistance during contact with elements of the shell. Examples include polymeric materials having molecular weights ranging from about $5.0 \times 10E5$ grams/mol to about $6.0 \times 10E6$ grams/mol more particularly about $4.0 \times 10E6$ grams/mol, modulus of elasticity ranging from about 0.7 to about 3.0 GPa, and cross linking density ranging from 0 to about 50% (as measured by the swell ratio). Examples of such polymers include ultra-high molecular weight polyethylene (UHMWPE), which may be crosslinked or uncrosslinked, polyetherether ketone (PEEK), and the like. Other examples include metallic materials, such as cobalt-chrome alloys, and ceramic materials, such as alumina or zirconia.

The second material, as used in this embodiment, is an elastomeric material such as a polyurethane, more particularly a polycarbonate polyurethane (e.g., an aromatic polycarbonate polyurethane) or polysiloxane polyurethane; a silicone; a polyolefin such as polyethylene; or a hydrogel. Desirably, the second material has a hardness of at least about 75A Durometer (Shore scale), more particularly, a hardness ranging from about 80A to about 65D.

In one embodiment of a central body for use in an endoprosthesis in connection with articulating shells, the central body contains a central component formed from the second material, disposed between two outer components formed from the first material. These outer components form wear resistant "caps" that provide wear surfaces for contact with the articulating shells. The thickness of the caps is sufficient to provide adequate useful life for the endoprosthesis, but not so thick as to significantly decrease the level of elasticity provided by the resilient second material. Typical thicknesses for the layers of first material range from about 0.25 mm to about 7 mm.

The caps desirably have a geometry that provides a smooth outer bearing surface for contact with the shells of the endoprosthesis, as indicated above. In addition, the cap geometry may contain elements that help to retain the cap in ideal alignment with the central component (i.e., the elastomeric "core" of the central body), or may be simply be inset into the central component and held in place by compressive forces (either those exerted on the cap by the resilient material surrounding the inset, or those exerted on the cap by the shells of the endoprosthesis or both).

These concepts can be further understood by reference to the drawings. FIG. 1 through FIG. 4 show a central body particularly suited for use in an articulating endoprosthesis for use as a lumbar intervertebral endoprosthesis. FIG. 5 through FIG. 7 illustrate a central body particularly suited for use in an articulating endoprosthesis for use as a cervical intervertebral disc endoprosthesis. It will be understood, however, that the central body concepts illustrated are not limited to use in endoprostheses implanted into these levels alone, and in fact are not limited to intervertebral endoprostheses, but can be used or adapted for use in other endoprostheses, e.g., for implantation in other joints.

Figure 2:
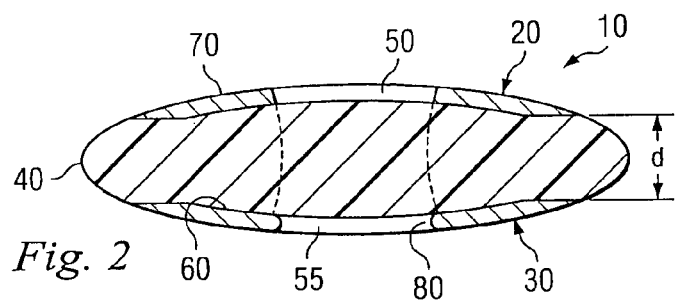
FIG. 2 is a cross-sectional view along line A-A in FIG. 1.

FIG. 1 is a perspective view and FIG. 2 is the corresponding cross-sectional view along line A-A, illustrating an embodiment of the invention wherein the central body 10, which is adapted to be disposed between two articulating shells (not shown), has a first outer element or "cap" 20, a second outer element or "cap" 30, both made of wear resistant first material, and a resilient central element or "core" 40, made of resilient second material. Central openings 50, 55 are adapted to cooperate with a retaining element disposed on the inner surface of the corresponding shell (not shown) to limit the motion of the shell with respect to the central body.

The distance d between the closest portions (as illustrated, the edges) of first cap 20 and second cap 30 should be sufficient that the amount of resilient second material therebetween can provide the desired height under expected load and compression conditions before the edges of the caps come into contact. As illustrated, inner surfaces 60 of caps 20 and 30 are curved, and the radius of this curvature may be the same as or different from that of the outer surfaces 70 of the caps 20, 30, but corresponds closely to the radius of curvature of the surface of core 40. As compressive stress is exerted against the outer surfaces of caps 20, 30, this stress will be transferred to the core 40. Core 40 will tend to respond to this stress by undergoing strain. Because the second material forming core 40 is resilient, some of this strain will be in the lateral direction, toward the edges of the core. The curved inner surfaces of the stiffer caps tend to limit this lateral strain, and to resist shear stresses in the core.

FIG. 2 illustrates an optional feature of the invention, namely that central opening 55 can extend some distance 80 into core 40. This allows the use of a shell having retaining elements such as a retaining post having a reverse-taper or other geometry with some form of lateral extension near the tip thereof, and which will extend into central opening 55 (and which can be, e.g., snap-fit into central opening 55). This retaining post geometry combined with the extension of the central opening 55 into core 40, can reduce the generation of impact debris, because the wider diameter edge of the retaining post comes into contact with the resilient second material of the core, rather than the harder first material of the cap. The internal geometry of the central opening can be adapted to provide the desired limit of motion for the articulation of the endoprosthesis. It will be understood that this feature is illustrated with respect to only one central opening for ease of understanding and comparison, and if the feature is included, it would likely be included with respect to both central openings, be they through holes, blind holes or any combination.

Figure 3A:
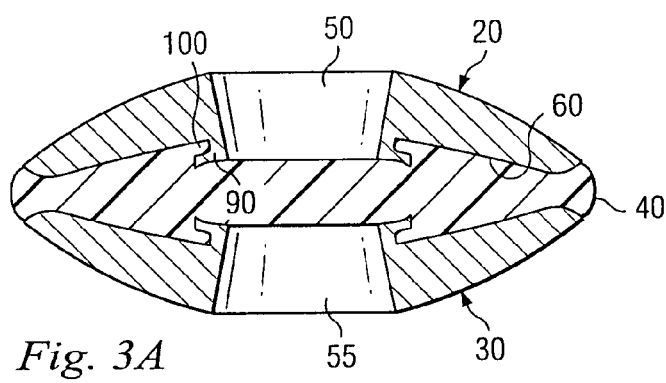
FIGS. 3A and 3B are cross-sectional views of alternative embodiments of composite central body according to the invention, showing two different thicknesses for various elements of the central body, and various retention features.
Figure 3B:
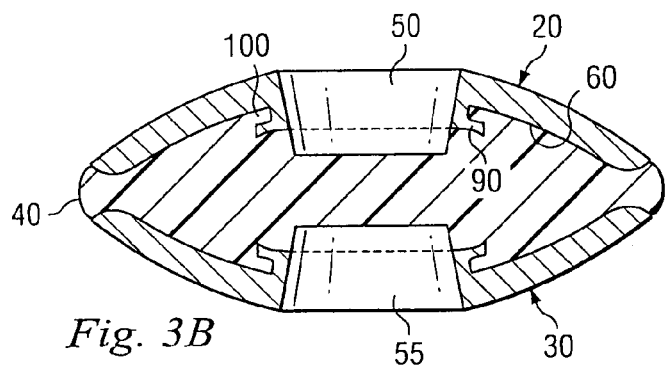

FIGS. 3A and 3B disclose two alternative embodiments of a central body according to the invention. In FIG. 3A, caps 20, 30 are relatively thick, while core 40 is relatively thin, as compared to the central body shown in FIG. 3B. Inner surface 60 of the caps shown in FIG. 3A has less curvature than that of the caps shown in FIG. 3B. However, both embodiments show a retaining feature for mechanically locking the caps to the core. The inner surfaces of caps 20, 30 form circumferential lip flanges 90 around central openings 50, 55. The resilient core 40 contains corresponding circumferential lip flanges 100 (which may be formed during an insert molding process). The lip flanges 90, 100 engage to hold caps 20, 30 into close contact with core 40, and help to prevent detachment and/or delamination.

FIGS. 3a and 3b also illustrate another optional feature of the invention, namely that the thickness of caps 20, 30 can vary in the radial direction. As illustrated, caps 20, 30 are thicker near central openings 50, 55 than near the peripheral edge. Thicker caps can provide an increase in durability and wear resistance, but will likely result in a decrease in resiliency, since for a given volume of central body and a given second material, there will be a smaller amount of second material present to provide resiliency if the thickness of the caps in increased. Caps that are thicker toward the central openings 50, 55 provide increased durability in areas of the device more likely to come into contact with the shell or retaining devices of the endoprosthesis. By making the caps thinner toward their periphery, a greater proportion of the thickness of the endoprosthesis is made of the more resilient second material in regions of the endoprosthesis where avoiding contact between the caps is of greater concern.

Figure 4:
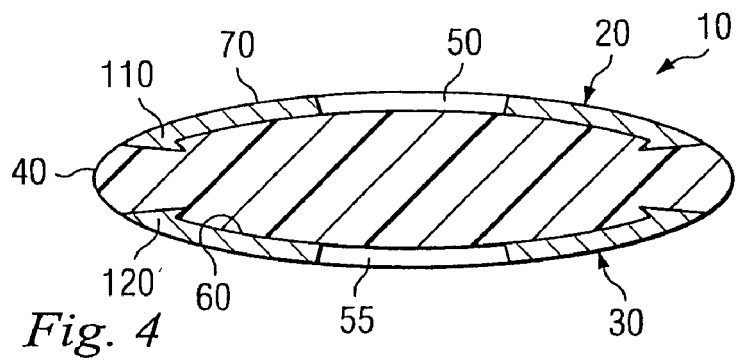
FIG. 4 is another cross-sectional schematic view of an embodiment of the central body, wherein the outer elements contain retention features along the outer rim of the outer elements that retain the resilient material when it is under compression.

FIG. 4 illustrates an alternative embodiment of central body 10, having lip flanges 110, 120 located on the outer rim of the caps 20, 30, and in the corresponding portion of core 40. As the core is compressed, the lip flanges help to limit shearing strain of the core material relative to the cap, and help to secure the caps to the core.

Figure 5A:
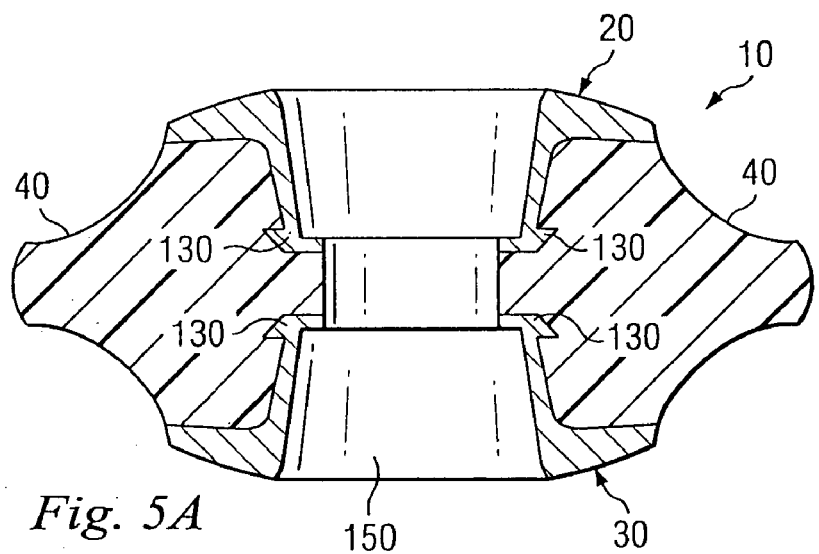
FIGS. 5A and 5B are cross sectional views of two alternative embodiments of composite central body according to the invention.

FIG. 5A illustrates another embodiment of a central body 10 according to the invention and having caps 20, 30, and core 40 disposed therebetween. Caps 20, 30 contain retention elements that are lip flanges 130 disposed around the edge of central opening 150 (not shown in FIG. 5A). These flanges contain axially extending element 135 and radially extending element 137, and cooperate with corresponding notches formed in core 40 to help prevent caps 20, 30 from detaching from core 40. Either the caps or the core may be insert molded, so that the flanges and corresponding notches are closely fit, or the components may be formed separately and assembled as in a snap-fit arrangement.

Figure 5B:
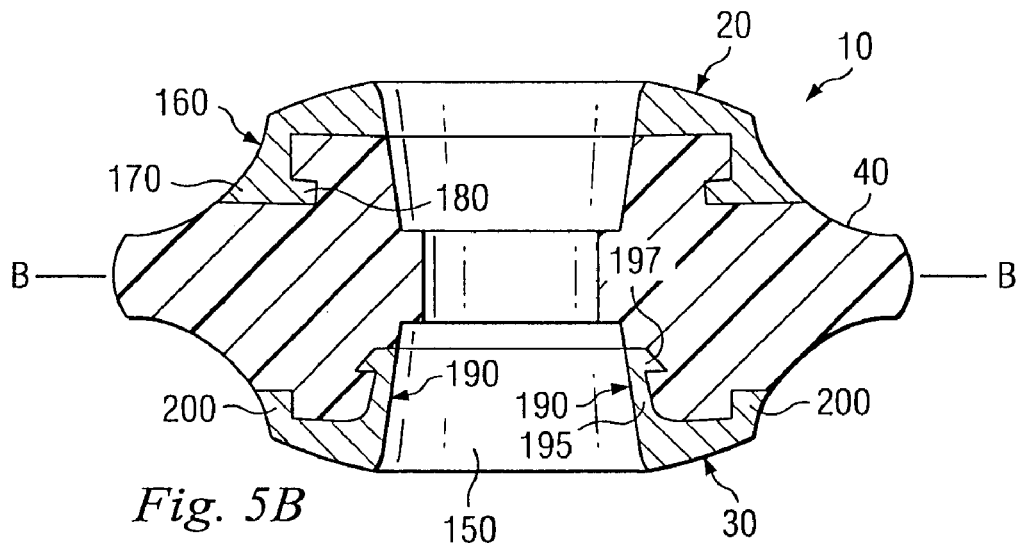

FIG. 5B is a cross-sectional view that schematically illustrates two additional embodiments of retention features in central bodies according to the invention. Cap 20 has flange 160 disposed along its outer edge. Flange 160 contains an axially extending portion 170 and a radially inward extending portion 180. Cap 30 contains radially extending lip flange 190 disposed around the edge of the central opening 150, and axially extending element 200 disposed around the outer edge of cap 30. Lip flange 190 contains axially extending element 195 and radially extending element 197. It will be understood that FIG. 5B is schematic, and that for ease of manufacturing, both caps 20, 30 may have the same retaining features, and may in fact be mirror images across reflecting plane B-B.

These retention elements cooperate with corresponding notches formed in core 40 to retain caps 20, 30 in contact with core 40. It will also be understood that combinations of portions of these retention elements can be used. For example, retention element 160 could be used in combination with retention element 190, replacing retention element 200.

FIG. 6A illustrates an embodiment of a central body wherein the outer caps 20, 30 are formed of the first material, and are considerably thicker than the caps shown in FIG. 1 through FIG. 5. The outer caps 20, 30 include recesses 210 for retaining and engaging with the central body 40, which in the present embodiment is an O-ring or toroid of the second, more resilient material. Since the upper and lower caps 20, 30 are larger than in the previously-described embodiments, and the first material thereby comprises a greater proportion of the endoprosthesis 10, exceptional wear resistance can be provided. This embodiment provides additional wear resistance along the outer concave surfaces of the endoprosthesis 10, while still providing for sufficient resiliency.

FIG. 6B illustrates an alternative embodiment wherein upper and lower caps 20, 30, respectively, are held together by a snap-fit. In the illustrated embodiment, the cap 30 includes a lip 212 for engaging with a flexible protrusion 214 of the cap 20. In this way, the endoprosthesis 10 can be assembled with the central body 40 inside the recesses 212 and secured with the snap-fit engagement of the lip 212 and protrusion 214. Also, even after engaged, the caps 20, 30 can be pressed closer to each other, such as during normal loading from use in the spine.

FIGS. 7A and 7B illustrate yet another embodiment of the invention. The upper cap 20 includes four sleeves 210 for slidably engaging with four corresponding posts 220 of the lower cap 30. The posts 220 and sleeves 216 can be positioned within four corresponding openings 222 in the resilient core 40. As described below, the resilient portion 40 can be introduced between upper and lower portions 20, 30 by various techniques, e.g., by insert molding. The posts 220 and sleeves 210 help to prevent any lateral relative motion between the two caps 20, 30, while allowing longitudinal motion 224 between the two. In this way, compressive motion can be provided while maintaining lateral rigidity.

In another embodiment of the invention, the central body can contain a central component formed from the first material, disposed between outer components formed from the second material. Such an arrangement might be desirable, e.g., in a device where a portion of the central component extends radially from the center of the endoprosthesis, forming a circumferential ridge, in order to limit or prevent contact between the edges of the shells, e.g., when the endoprosthesis meets or exceeds its desirable range of motion. In such a device, the radial extension of the central component will contact the shell edge(s), which can result in wear. Making some or all of this portion of the device from a wear resistant material (i.e., the first material) can limit or avoid generation of wear debris that results from subjecting the endoprosthesis to extreme range of motion.

In the embodiments of the invention disclosed above, the central body can be made by a variety of techniques, such as insert molding, injection molding and machining and assembly, and the like. The design of the central body, as well as the difference in physical properties of materials, makes insert molding particularly attractive. For example, the embodiment of the invention wherein wear resistant caps are to be disposed around an elastomeric core can be made by forming the end caps using any acceptable technique (e.g., injection molding followed by machining), disposing the harder, higher melting caps into an insert mold, and injecting molten elastomeric material into the mold cavity between the caps As an example, UHMWPE is formed into caps, which are machined as necessary to obtain the desired shape, and introduced into the mold cavity of an injection molding machine. The mold is then closed, and polycarbonate polyurethane material (e.g., Chronoflex C80A) is introduced into the mold cavity between the caps at a temperature of about 450° F. and a range of pressure correlating the geometry of the cavity and rate of injection. Temperature in the mold is monitored and adjusted as needed, and after approximately 1-2 minutes, the mold is opened and the central body is withdrawn and any flashing removed. The resulting central body can then be assembled into an endoprosthesis by disposing it between two compatibly shaped endplate shells.

The endoprosthesis can be provided as part of a kit, which may include one more surgical instruments designed to locate and prepare the joint space, and implant the endoprosthesis therein. Suitable instruments for preparing an intervertebral disc space and implanting therein an intervertebral endoprosthesis are disclosed in U.S. Ser. No. 09/923,891, filed Aug. 7, 2001. The surgical method, as described in the cited patent application, includes precisely locating the site of the endoprosthesis, performing at least a partial discectomy, preparing the endplates of the vertebral bodies to correspond to the geometry of the outer surface of the shell, and implanting the endoprosthesis. Similar procedures can be used to implant endoprostheses in other joints.

What is claimed is:

1. A body member for use in combination with a shell to form an implantable endoprosthesis, the body member comprising:
    a first component having an articular surface for articulated sliding movement with the shell, the first component formed from a wear resistant first material, the first material comprising a polymer having a first hardness; and
    a second component formed from a resilient second material for absorbing compressive and shear forces imparted upon the implantable endoprosthesis, the second material comprising a polymer having a second hardness softer than the first hardness, the second hardness being approximately 80 Shore A;
    wherein the second component is disposed between the first component and a third component also formed from the first material, the third component having an articular surface for articulated sliding movement with the shell;
    wherein the body member is adapted to articulate with respect to the shell such that one or more surfaces of the shell come into sliding contact with the articular surfaces of the first and third components during articulation.

2. The body member of claim 1, wherein the polymer of the first material comprises a polyethylene.

3. The body member of claim 2, wherein the polyethylene has a molecular weight ranging from about $5.0 \times 10E5$ grams/mol to about $6.0 \times 10E6$ grams/mol.

4. The body member of claim 3, wherein the polyethylene has a modulus of elasticity ranging from about 0.7 to about 3.0 Gpa.

5. The body member of claim 4, wherein the polyethylene is cross-linked to an extent ranging between about 0% to about 50%, as measured by a swell ratio.

6. The body member of claim 1, wherein the polymer of the first material comprises a polyetheretherketone (PEEK).

7. The body member of claim 1, wherein the polymer of the second material is selected from the group consisting of polyurethanes, silicones, and polyolefins.

8. The body member of claim 7, wherein the polymer of the second material is a polycarbonate polyurethane.

9. The body member of claim 1, wherein the first and third components each include a recess for receiving one or more projections of the shell to limit translational sliding movement of the body member with respect to the shell.

10. The body member of claim 9, wherein the first component comprises a projection for snap-fit engagement with a recess of the third component.

11. The body member of claim 10, wherein snap-fit engagement between the first and third component limits separation of the first and third components away from one another while allowing the first and third components to be compressed towards one another.

12. The body member of claim 11, wherein the second component resiliently limits compression of the first and third components towards one another.

13. The body member of claim 12, wherein the second component includes a central opening extending therethrough for receiving the projection of the first component to facilitate the snap-fit engagement of the first and third components.

14. A body member for use with a shell structure of an implantable endoprosthesis, comprising:
a first portion having a first convex surface configured to articulate with a first concave surface of the shell structure, the first portion formed from a first wear-resistant material having a first hardness, the first portion having a thickness between about 0.25 mm and about 0.75 mm;
a second portion having a second convex surface configured to articulate with a second concave surface of the shell structure, the second portion formed from a second wear-resistant material having a second hardness, the second portion having a thickness between about 0.25 mm and about 0.75 mm; and
a third portion positioned at least partially between the first and second portions to avoid contact with the shell structure, the third portion formed from a resilient material having a third hardness, the third harness being softer than the first and second hardnesses and being between about 75 Shore A and 85 Shore A, the resilient material for absorbing compressive and shear forces imparted upon the implantable endoprosthesis, the resilient material having a thickness greater than the thicknesses of the first and second portions;
wherein at least the first wear-resistant material and the resilient material comprise a polycarbonate polyurethane.

15. The body member of claim 14 wherein the first wear-resistant material and the second wear-resistant material are the same.

16. The body member of claim 14 wherein the first portion further comprises an opening adapted to receive a first projection of the shell structure.

17. The body member of claim 16 wherein the second portion further comprises an opening adapted to receive a second projection of the shell structure.

18. The body member of claim 14 wherein the first portion further comprises a first retention member for securing the first portion to the third portion.

19. The body member of claim 18 wherein the second portion further comprises a second retention member for securing the second portion to the third portion.

20. A body member for use with a bone-engaging shell structure of an implantable endoprosthesis, the body member comprising:
a first portion having a first convex surface configured to articulate with a first concave surface of the shell structure and a plurality of generally cylindrical sleeves extending opposite the first convex surface, the first portion formed from a first wear-resistant material having a first hardness;
a second portion having a second convex surface configured to articulate with a second concave surface of the shell structure and a plurality of generally cylindrical posts extending opposite the second convex surface and slidably engaged with the plurality of sleeves of the first portion to limit translational movement between the first and second portions while allowing compressive movement between the first and second portions towards and away from one another, the second portion formed from a second wear-resistant material having a second hardness; and
a third portion positioned at least partially between the first and second portions such that the first and second portions space the third portion from the shell structure, the third portion including a plurality of openings for receiving the plurality of sleeves and posts of the first and second portions, the third portion formed from a resilient material having a third hardness for absorbing compressive and shear forces imparted upon the implantable endoprosthesis, the third hardness being softer than the first and second hardnesses;
wherein at least the first wear-resistant material, second wear-resistant material, and the resilient material each comprise a polycarbonate polyurethane;
wherein the first and second components each include a recess for receiving one or more projections of the shell structure to limit translational movement of the body member with respect to the shell structure.

* * * * *

UNITED STATES PATENT AND TRADEMARK OFFICE
CERTIFICATE OF CORRECTION

PATENT NO. : 7,601,174 B2 Page 1 of 1
APPLICATION NO. : 10/600052
DATED : October 13, 2009
INVENTOR(S) : Kelly et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 610 days.

Signed and Sealed this

Fifth Day of October, 2010

David J. Kappos
*Director of the United States Patent and Trademark Office*